United States Patent [19]

Lavanish

[11] 4,264,353

[45] * Apr. 28, 1981

[54] 3-[5-[1-(4-HALOPHENOXY)ALKYL, ALKYNYL, ALKENYL, OR HALOALKYL]-1,3,4-THIADIAZOL-2-yl]-4-HYDROXY-1-METHYL-2-IMIDAZOLIDI-NONES

[75] Inventor: Jerome M. Lavanish, Akron, Ohio

[73] Assignee: PPG Industries, Inc., Pittsburgh, Pa.

[*] Notice: The portion of the term of this patent subsequent to Aug. 19, 1997, has been disclaimed.

[21] Appl. No.: 45,536

[22] Filed: Jun. 4, 1979

[51] Int. Cl.$^3$ .................... A01N 43/82; C07D 417/04
[52] U.S. Cl. ........................................ 71/90; 548/137; 548/138; 548/139; 548/140
[58] Field of Search ............................ 71/90; 548/137

[56] References Cited

U.S. PATENT DOCUMENTS

| | | | |
|---|---|---|---|
| 3,901,904 | 8/1975 | Krenzer | 548/137 |
| 3,904,640 | 9/1975 | Krenzer | 548/137 |
| 3,920,674 | 11/1975 | Krenzer | 548/137 |
| 3,964,895 | 6/1976 | Krenzer | 71/90 |
| 4,028,375 | 6/1977 | Krenzer | 548/137 |

*Primary Examiner*—Paul M. Coughlan, Jr.
*Attorney, Agent, or Firm*—Edward J. Whitfield; Robert J. Grassi

[57] ABSTRACT

The disclosed compounds, such as 3-[5-[1-(4-chlorophenoxy)ethyl]-1,3,4-thiadiazol-2-yl]-4-hydroxy-1-methyl-2-imidazolidinone, are useful for preemergence and postemergence control of weeds, such as jimsonweeds.

25 Claims, No Drawings

3-[5-[1-(4-HALOPHENOXY)ALKYL, ALKYNYL, ALKENYL, OR HALOALKYL]-1,3,4-THIADIAZOL-2-yl]-4-HYDROXY-1-METHYL-2-IMIDAZOLIDINONES

BACKGROUND OF THE INVENTION

1. FIELD OF THE INVENTION

The invention relates to substituted 1,3,4-thiadiazol-2-yl-4-hydroxy-1-methyl-2-imidazolidinone, particularly to the 3-[5-[1-(4-chlorophenoxy alkyl,-alkynyl-alkenyl, -or haloalkyl substituted)-1,3,4 thiadiazol-2-yl]-4-hydroxy-1-methyl-2-imidazolidinone compounds.

2. DESCRIPTION OF THE PRIOR ART

Imidazolidinones, as a class, are described in patents and chemical literature; none of which, however, teaches or discloses the novel herbicidal compounds described herein and their use to control the weeds described herein.

SUMMARY OF THE INVENTION

The invention described herein concerns compounds graphically represented by Formula I.

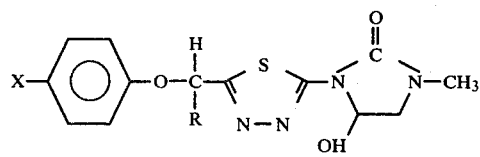

wherein:

X is a chlorine, bromine, fluorine or iodine, and;

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 2-bromoethyl; the intermediates graphically represented by Formulas III, IV, and V,

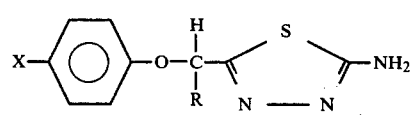

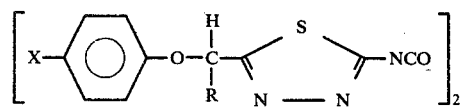

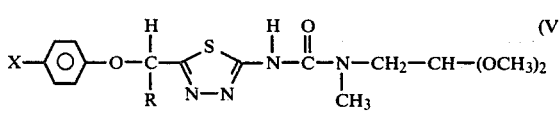

wherein: X and R are defined as herein, as well as the process for making compounds of the described formulas. The compounds of Formula I are particularly useful for controlling weeds postemergence and preemergence and are selective to other weeds both postemergence and preemergence at low rates of applications. Particularly the compounds wherein X is chlorine and R is methyl or ethyl. For example, the compound where X is chlorine and R is methyl is useful for controlling, jimsonweed, crabgrass, johnsongrass, coffeeweed, velvetleaf, wild oats and barnyardgrass, at preemergence rates as low as two pounds per acre.

DESCRIPTION OF THE PREFERRED EMBODIMENT

The novel agriculturally useful compounds described herein may be graphically represented by Formula I:

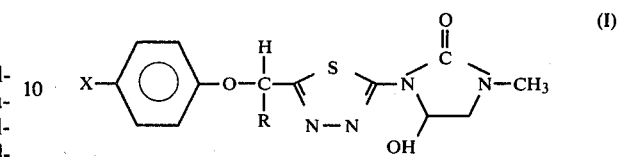

wherein:

X is chlorine, bromine, fluorine, or iodine, and

R is an alkyl of up to four carbon atoms, an alkenyl of up to three carbon atoms, an alkynyl of up to three carbon atoms, or a haloalkyl selected from the group consisting of chloromethyl, bromomethyl, 2-chloroethyl, and 3-bromoethyl.

Examples of compounds represented by Formula I are:

3-[5-[1-(4-chlorophenoxy)ethyl]-1,3,4-thiadiazol-2-yl]-4-hydroxy-1-methyl-2-imidazolidinone 3-[5-[1-(4-bromophenoxy)-2-bromoethyl]-1,3,4-thiadiazol-2-yl]-4-hydroxy-1-methyl-2-imidazolidinone.

3-[5-[1-(4-fluorophenoxy)-2-bromoethyl]-1,3,4-thiadiazol-2-yl]-4-hydroxy-1-methyl-2-imidazolidinone.

3-[5-[1-(4-iodophenoxy)-3-chloropropyl]-1,3,4-thiadiazol-2-yl]-4-hydroxy-1-methyl-2-imidazolidinone.

3-[5-[1-(4-chlorophenoxy)-3-bromopropyl]-1,3,4-thiadiazol-2-yl]-4-hydroxy-1-methyl-2-imidazolidinone.

3-[5-[1-(4-bromophenoxy)-2-propynyl]-1,3,4-thiadiazol-2-yl]-4-hydroxy-1-methyl-2-imidazolidinone.

3-[5-[1-(4-fluorophenoxy)-2-butynyl]-1,3,4-thiadiazol-2-yl]-4-hydroxy-1-methyl-2-imidazolidinone.

3-[5-[1-(4-iodophenoxy)-3-butynyl]-1,3,4-thiadiazol-2-yl]-4-hydroxy-1-methyl-2-imidazolidinone.

3-[5-[1-(4-chlorophenoxy)-2-propenyl]-1,3,4-thiadiazol-2-yl]-4-hydroxy-1-methyl-2-imidazolidinone.

3-[5-[1-(4-bromophenoxy)-2-butenyl]-1,3,4-thiadiazol-2-yl]-4-hydroxy-1-methyl-2-imidazolidinone.

3-[5-[1-(4-fluorophenoxy)-2-chloroethyl]-1,3,4-thiadiazol-2-yl]-4-hydroxy-1-methyl-2-imidazolidinone.

3-[5-[1-(4-iodophenoxy)-2-bromoethyl]-1,3,4-thiadiazol-2-yl]-4-hydroxy-1-methyl-2-imidazolidinone.

3-[5-[1-(4-chlorophenoxy)-3-chloropropyl]-1,3,4-thiadiazol-2-yl]-4-hydroxy-1-methyl-2-imidazolidinone.

3-[5-[1-(4-bromophenoxy)-3-bromopropyl]-1,3,4-thiadiazol-2-yl]-4-hydroxy-1-methyl-2-imidazolidinone.

3-[5-[1-(4-fluorophenoxy)-3-butenyl]-1,3,4-thiadiazol-2-yl]-4-hydroxy-1-methyl-2-imidazolidinone.

3-[5-[1-(4-iodophenoxy)-1-pentenyl]-1,3,4-thiadiazol-2-yl]-4-hydroxy-1-methyl-2-imidazolidinone.

3-[5-[1-(4-chlorophenoxy)-1-(3-methylbutyl)]-1,3,4-thiadiazol-2-yl]-4-hydroxy-1-methyl-2-imidazolidinone.

3-[5-[1-(4-bromophenoxy)-2-(2-methylbutyl)]-1,3,4-thiadiazol-2-yl]-4-hydroxy-1-methyl-2-imidazolidinone.

3-[5-[1-(4-fluorophenoxy)-1-(2,2-dimethylpropyl)]-1,3,4-thiadiazol-2-yl]-4-hydroxy-1-methyl-2-imidazolidinone.

3-[5-[1-(4-iodophenoxy)-1-butyl]-1,3,4-thiadiazol-2-yl]-4-hydroxy-1-methyl-2-imidazolidinone.

3-[5-[1-(4-chlorophenoxy)-(2-methylpropyl)]-1,3,4-thiadiazol-2-yl]-4-hydroxy-1-methyl-2-imidazolidinone.

3-[5-[1-(4-bromophenoxy)propyl]-1,3,4-thiadiazol-2-yl]-4-hydroxy-1-methyl-2-imidazolidinone.

Although all of the compounds described herein are useful for the purpose described herein, some compounds are more useful than others. Those compounds in which R is an alkynyl, as defined herein, are of a general utility, while those compounds in which R is an alkenyl, as defined herein, are of better utility. Those compounds in which R is a haloalkyl described herein are of high utility and of these, the preferred compounds are those in which R is chloromethyl or bromomethyl. Those compounds in which R is an alkyl described herein, are highly preferred and especially preferred are compounds in which the alkyl is methyl, ethyl, or propyl. X is preferably, chlorine or bromine, and chlorine is most preferred. The following compounds are the most preferred: 3-[5-[1-(4-chlorophenoxy)propyl]-1,3,4-thiadiazol-2-yl]-4-hydroxy-1-methyl-2-imidazolidinone, and 3-[5-[1-(4-chlorophenoxy)ethyl]-1,3,4-thiadiazol-2-yl]-4-hydroxy-1-methyl-2-imidazolidinone.

SYNTHESIS OF THE COMPOUNDS

The synthesis of the compound preceeds according to the general reactions 1, 2, 3, and 4, shown below:

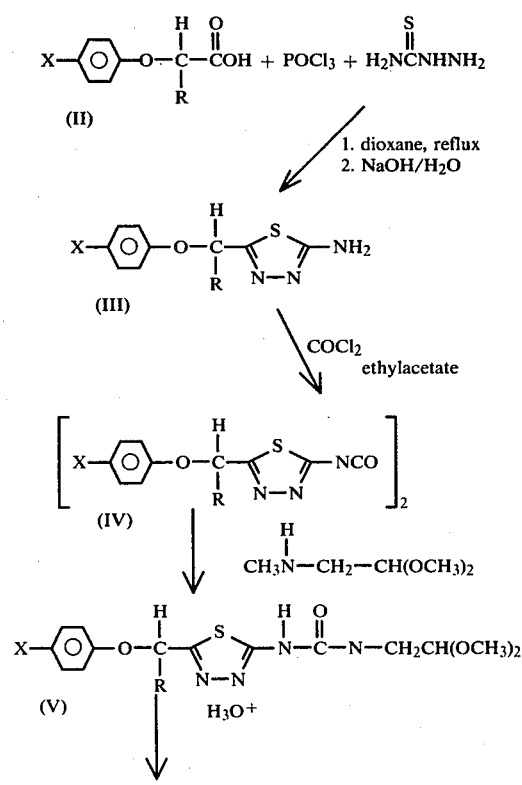

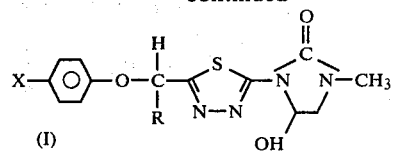

PREPARATION OF 5-SUBSTITUTED 2-AMINO-1,3,4-THIADIAZOLE

The proper alpha substituted carboxylic acid graphically represented by Formula II, wherein R and X are as described herein (typically 0.4–0.5 moles), an equimolar amount of thiosemicarbazide, and 30-milliliters of dry dioxane, are charged into a hundred milliliter reactor equipped with a thermometer, an efficient stirrer, pressure equilized, addition funnel, and a condenser-drying tube. The additional funnel is charged with approximately 10 percent excess of phosphorus oxychloride which is added drop wise so as to maintain a reaction temperature of 85°–95° C. and reaction occurs as shown by reaction equation 1. The mixture is then heated to reflux for about 1 hour, after which the solvent is flashed off using a vacuum such as a water aspirator. Water (50 milliliters) is added to the residue to give an emulsion which is then made basic with a 50% sodium hydroxide solution. In those instances that a solid product is obtained (graphically represented by formula III, wherein X and R are as described herein) the product is isolated by filtration, and recrystalized when necessary. In other cases, the reaction mixture is extracted with ether, the ether layer is separated from the heavier layers, dried over magnesium sulfate, filtered and concentrated under vacuum to give the crude product represented as a viscous oil.

PREPARATION OF THE ISOCYANATE DIMERS

Five to 10 grams of the appropriate 2-amino-1,3,4-thiadiazole (graphically represented by Formula III is added to a solution of phosgene in ethylacetate, (or other suitable solvent) prepared by saturating 50–100 milliliters of solvent with phosgene at room temperature then adding another 50–100 milliliters of solvent. The mixture is allowed to stir overnight at room temperature as shown by reaction equation 2 and then purged with nitrogen or argon to remove the unreacted phosgene. In those cases where a solid was obtained the product (graphically represented by Formula IV which is an isocyanate dimer of the appropriate substituted 1,3,4-thiadiazole) was isolated by filtration and dried. In cases where no solid product is evident, the reaction mixture may be topped under vacuum to give the product as a viscous oil or glass.

PREPARATION OF ACETAL UREAS

The appropriate isocyanate dimer of Formula IV and an equivalent amount of methylaminoacetaldehyde dimethylacetal were heated to reflux (5–15 minutes) in an inert solvent such as ether, benzene, or toluene, and the reaction proceeded as shown by reaction equation 3 so as to form the product graphically represented by Formula V. Some products may be produced as crystals directly from solution, but others may be induced by addition of hexane. The product represented by graphic Formula V may be purified such as by washing with ether, or hexane or recrystalized from hexane/benzene or from ether/benzene, or from ether/chloroform/benzene solutions. Those products or compounds that are represented by Formula V obtained as oils need not be purified.

PREPARATION OF THE COMPOUNDS OF FORMULA I

The appropriate acetal urea of Formula V (approximately three to four grams) is added to 150-200 milliliters of water containing 1.5-2 milliliters of concentrated hydrochloric acid. The mixture is stirred vigorously and heated to reflux, and reaction proceeds as shown by reaction equation 4. The hydrolysis is monitored by thin layer chromatography (alumina-ethylacetate) until complete, and the product containing a compound of Formula I forms. The product, in some cases, may be crystalized directly from the reaction mixture upon cooling. In other cases, the compounds of Formula I are extracted with chloroform and isolated by stripping the solvent under vacuum. Those compounds which solidify upon concentration are further purified. In some cases, the compounds may be used directly as obtained. In other cases, crystallization is induced by seeding an ether solution with a related compound, and the crystal formed may be further purified.

EXAMPLE I

The following example illustrates the synthesis of the compounds described herein.

SYNTHESIS OF
3-[5-[1-(4-chlorophenoxy)ethyl]-1,3,4-thiadiazol-2-yl]-4-hydroxy-1-methyl-2-imidazolidinone a. formation of 5-[1-(4-chlorophenoxy)ethyl]-2-amino-1,3,4-thiadiazole

Into a 100 milliliter, 3-neck flask adapted with a Claisen adaptor, paddle stirrer, thermometer, an addition funnel and condensor, was charged with 10.0 grams (0.050 mole) of 2-(4-chlorophenoxy)propanoic acid, (4.6 grams, 0.050 mole) of thiosemicarbazide and 30 ml. of dioxane. The slurry was heated to 90 degrees centigrade and the addition funnel was charged with phosphorous oxychloride ($POCl_3$). The $POCl_3$(8.4 gram, 0.055 mole) was slowly added (for 30 minutes) while maintaining the temperature within 85-90 degrees centigrade. The resulting mixture was refluxed for 75 minutes and stood at ambient temperature for 16 hours. The flask was evacuated by using a water aspirator to remove volatiles (HCl, $POCl_3$ and some dioxane) at sixty degrees centigrade and then the solution was cooled. Fifty (50) milliliters of water was added and 50 percent solution of NaOH was also added until the pH of the solution was 10; a solid precipitate formed. The solid precipitate was filtered off, washed with water, then dried in a vacuum oven at 70 degrees centigrade to white crystals which were recrystallized from the minimum amount of $H_2O$/ethanol mixture, filtered and then dried in a vacuum oven at 80 degrees centigrade to white crystals of 5-[1-(4-chlorophenoxy) ethyl]-2-amino-1,3,4-thiadiazole. (Melting point 162-166 degrees centigrade).

b. Formation of 5-[1-(4-chlorophenoxy)ethyl]-1,3,4-thiadiazol-2-yl isocyanate dimer A 500 millileter, 3-neck flask equipped with a magnetic stirrer, thermometer, dry ice condensor/drying tube and inlet from a phosgene ($COCl_2$) tank via a calibrated rotometer was charged with 50 milliliters of ethylacetate saturated with phosgene at 20° C. (approximately 0.5 mole of phosgene). Additional 100 ml. of ethylacetate was added; (8.9 grams of 5-[1-(4-chlorophenoxy) ethyl]-2-amino-1,3,4-thiadiazole, (prepared above) at a temperature from 0° C. to room temperature was added. The resulting solution was stirred for 17 hours with formation of an emulsion, and then the flask was purged with nitrogen until no $COCl_2$ was detected. The solution was filtered through a Whatman #42 filter paper to yield a slightly cloudy solution which was topped at 60 degrees centigrade with a roto-vac to form 9.2 grams of a pale yellow goop of 5-[1-(4-chlorophenoxy)ethyl]-1,3,4-thiadiazol-2-yl isocyanate dimer.

c. Formation of 3-[5-[1-(4-chlorophenoxy)ethyl]-1,3,4-thiadiazol-2-yl]-1-methyl-1-(2,2-dimethoxyethyl)urea At ambient temperatures 3.9 grams (0.033 mole) of methylaminoacetaldehyde dimethylacetate was slowly added to a 30 ml. benzene solution containing 9.2 grams (0.033 mole) of the 5-[1-(4-chlorophenoxy)ethyl]-1,3,4-thiadiazol-2-yl isocyanate dimer (prepared above). The resulting solution was refluxed for 30 minutes to form a yellow solution and then cooled and topped with a roto-vac at 60 degrees centigrade to 12.4 grams of a viscous yellow oil which crystallized upon standing. The entire sample was recrystallized from a minimum amount of ethylacetate/hexane solution. The crystals were filtered off, and dried in a vacuum oven at 80 degrees centigrade to give 8.3 grams of fluffy white crystals of 3-[5-[1-(4-chlorophenoxy)ethyl-]-1,3,4-thiadiazol-2-yl]-1-methyl-1-1(2,2-dimethoxyethyl)urea. Melting point 116-118 degrees centigrade.

d. Synthesis of 3-[5-[1-(4-chlorophenoxy)ethyl]-1,3,4-thiadiazol 2-yl]-1-methyl-4-hydroxy-2-imidazolidinone A solution containing 3.0 grams of the 3-[5-[1-(4-chlorophenoxy)ethyl]-1,3,4-thiadiazol-2-yl]-1-methyl-(2,2-dimethoxyethyl)urea (prepared above) in 100 milliliter of water and 1 milliliter of concentrated hydrochloric acid (HCl) was refluxed for 15 minutes, then cooled and the aqueous phase was discanted off, and the gooey solid remaining was washed with water. Then 100 ml. of benzene was added and the remaining water was azeotroped off. Then the remaining solution topped in a roto-vac at 70 degrees centigrade to yield 3.1 gram of a yellow oil. The yellow oil was dissolved in 20 milliliter diethyl ether, and the solution crystallized. The crystals were removed by suction filter, and were dried in a vacuum oven at 80 degrees centigrade to yield 1.4 grams of white crystals containing 3-[5-[1-(4-chlorophenoxy)ethyl]-1,3,4-thiadiazol-2-yl]-1-methyl-4-hydroxy-2-imidazolidinone. Melting point 117-130 degrees centigrade. The crystals were refluxed in 10 milliliter of benzene, and then diethylene ether was added, and the solution upon standing formed crystals which removed by suction filtration, and were dried in a vacuum oven at 80 degrees centigrade to give 0.7 grams of white crystals of 3-[5-[1-(4-chlorophenoxy)ethyl]-1,3,4-thiadiazol-2-yl]-1-methyl-4-hydroxy-2-imidazolidinone. Melting point 147-149 degrees centigrade.

IR spectra (mull): C=O bond at 1715 $cm^{-1}$.

NHR (DMF-d$_7$)-7.24 δ(mult., 5H), 6.10 δ(mult.), 5.95 δ(quartet), 3.90 δ(doublet of doublets), 3.40 δ(mult., 1H) 2.92 δ(sing., 3H), 1.79 δ(doublet, 3H).

INTERMEDIATE COMPOUNDS

Although the other compounds described herein and represented graphically by Formulas III and IV possess no herbicidal properties, and compods of Formula V possess herbicidal properties, nevertheless, the compounds represented by the Formulas III, IV and V are very useful because they are intermediates for the synthesis of the novel compounds represented by Formula I.

APPLICATIONS OF THE COMPOSITIONS AGAINST WEEDS

The novel active compounds of Formula I are particularly valuable for weed control because they are toxic to many species and groups of weeds and are relatively nontoxic to many beneficial plants. The exact amount of one or more of the compounds required depends upon a variety of factors, including the hardiness of the particular weed species, the weather, the type of soil, the method of application, the kind of beneficial plants in the same area, and the like. Thus while the application of up to only about one or two ounces of active compound per acre may be sufficient for good control of a light infestation of weeds growing under adverse conditions, the application of 2 pounds or 10 pounds or more of an active compound of Formula I per acre may be required for good control of a dense infestation of hardy perennial weeds growing under favorable conditions.

a. EXAMPLES OF WEEDS WHICH MAY BE CONTROLLED BY THE COMPOUNDS DESCRIBED HEREIN

Weeds are undesirable plants growing where they are not wanted, having no economic value, and interfering with the production of cultivated crops, with the growing of ornamental plants, or with the welfare of livestock. Weeds may be classified as broadleaf or grassy weeds, a classification which includes many types of known weeds. It is believed that the compositions set forth herein, when applied in a herbicidally effective amount may control field pennycress, ryegrass, goosegrass, chickweed, purslane, smartweed, knotweed, wildbuckwheat, kochia, medic, corn cockle, ragweed, sow-thistle, croton, cuphea, dodder, fumitory, groundsel, hempnettle, knawel, spurge, spurry emex, jungle rice, pondweed, dogfennel, carpetweed, bedstraw, ducksalad, naiad, chestgrass, fall panicum, witchgrass, switchgrass, watergrass, teaseed, wild turnip, and sprangletop; biennials such as wild carrot, matricaria, wild barley, campion, chamomile, burdock, mullein, roundleaved mallow, bull thistle, houndstongue, moth mullein, and purple star thistle; or perennials such as white cockle, perennial ryegrass, quackgrass, canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cat-tail, winter-cress, horsenettle, nutsedge, milkweed, and sicklepod.

However, the important weeds of the genera against which the compounds of the invention are most effective postemergence at ten pounds per acre are: Sida, Datura, Brassica, Sorghum, Sesbania, Ipomoea, Avena, and Echinochloa. Weed species against which the compounds of the invention are most effective (postemergence) are: *Sida spinosa* (L) (teaweed), *Datura stramonium* (jimsonweed), *Brassica kaber* (wild mustard), *Sorghum halepense* (johnsongrass), *Sesbania* spp. (coffeeweed), *Ipomoea purpurea* (L) Roth (tall morningglory), *Aventa fatua* (wild oats), and *Echinochloa crusgalli* (barnyardgrass).

b. DESCRIPTION OF THE METHOD OF CONTROLLING WEEDS

As used herein and in the claims, the method of controlling the weeds comprises contacting the weeds with a herbicidally effective amount of a compound represented by the graphic formula described herein. The term "contacting the weeds" refers to any method of contacting the weeds, both preemergence (before the weeds appear) and/or postemergence (after the weeds appear), such as applying granules of the compound to the soil prior to emergence, or spraying a solution of the compound or compounds described by the general formula, or any other method known in the art by which the weeds are contacted either before they emerge or after they emerge, or both before and after they emerge, with one or more of the compounds represented by the general Formula (I) described herein. The phrase "herbicidally effective amount" refers to that amount required under the environmental conditions in order to effectively control, that is, by which the weeds are injured so as not to be able to recover from the application of the compound, or to be killed by the compound.

c. GENERAL APPLICATION OF THE COMPOUNDS

For practical use as herbicides, the compounds of this invention are generally incorporated into herbicidal formulations which comprise an inert carrier and a herbicidally toxic amount of a compound mentioned herein. Such herbicidal formulations enable the active compound to be applied conveniently to the site of the weed infestation in any desired quantity. These formulations can be solids such as dusts, granules, or wettable powders or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 millimeters. Wettable powders, which can be dispersed in water or oil to any desired concentration of the active compound, can be prepared by incorporating wetting agents into concentrated dust composition.

In some cases the active compounds are sufficiently soluable in common organic solvents such as kerosene or xylene so that they can be used directly as solutions in these solvents. Frequently, solutions of herbicides can be dispersed under superatmospheric pressure as aerosols. However, preferred liquid herbicidal formulations are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal formulation according to this invention is illustrated by the following example, in which the quantities are in parts by weight.

EXAMPLE II

PREPARATION OF A DUST

Product of Example I: 10
Powdered Talc: 90

The above ingredients are mixed in a mechanical grinder-blender and are ground until a homogeneous, freeflowing dust of the desired particle size is obtained. This dust is suitable for direct application to the site of the weed infestation.

d. MIXTURES OF COMPOUNDS ALONE OR IN MIXTURES

Although all of the compounds described herein and represented by the general formula described herein are useful as herbicides, some of these are preferred and are better for applications against weeds. In general, all of the compounds described herein may be used either alone or together in mixtures. When used in mixtures the amount or ratio of one compound to another may vary from 0.01 to 100.

e. MANNER OF APPLICATION OF THE COMPOUNDS OF THIS INVENTION

The compounds of this invention can be applied as herbicides in any manner recognized by the art. One method for the control of weeds comprises contacting the locus of said weeds with a herbicidal formulation comprised of an inert carrier and one or more of the compounds of this invention as an essential active ingredient, in a quantity which is herbicidally toxic to said weeds. The concentration of the new compounds of this invention in the herbicidal formulations will vary greatly with the type of formulations will comprise from about 0.05 to about 95 percent by weight of the active compounds of this invention. In a preferred embodiment of this invention, the herbicidal formulations can also comprise other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, desiccants, growth inhibitors, and the like in the herbicidal formulations heretofore described. These other materials can comprise from about 5 percent to about 95 percent of the active ingredients in the herbicidal compositions. Use of combinations of the present invention provide herbicidal formulations which are more effective in controlling weeds and often provide results unattainable with separate formulations of the individual herbicides.

f. EXAMPLES OF OTHER PESTICIDES AND HERBICIDES FOR COMBINATIONS

The other herbicides, defoliants, desiccants, and plant growth inhibitors, with which the compounds of this invention can be used in the herbicidal formulations to control weeds, can include: chlorophenoxy herbicides; such as 2,4-D, 2,4,5-T, MCPA, MCPB, 4-(2,4-DB), 2,4-DEB, 4-CPB 4-CPA, 5-CPP, 2,4,5-TB, 2,4,5-TES, 3,4-DA, silvex, and the like; carbamate herbicides such as IPC, CIPC, swep, barban, BCPC, CEPC, CPPC, and the like; thiocarbamate and dithiocarbamate herbicides such as CDEC, metam sodium, EPTC, diallate, PEBC, perbulate, vernolate and the like; substitued urea herbicides such as norea, siduron, dichloroal urea, chloroxuron cycluron, fenuron, monuron, monuron TCA, diuron, linuron, monolinuron, neburon, buturon, trimeturon, and the like; symmetrical triazine herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alphachloro-N-isopropyl-acetamide, 2-chloro-N-isopropylacetanilide, 4-(chloroacetyl) morpholine, 1-(lchloroacetyl)piperidine, and the like; chlorinated aliphatic acid herbicides such as TCA, dalapon, 2,3-dichloropropionic acid, 2,2,3-TPA, and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenyl-acetic acid, 2-methoxy-3,5,6-trichlorophenylacetic acid, 2,5-dichloro-3-nitrobenzoic acid, dual, metribuzin and the like; and such compounds as aminotriazole, maleic hydrazode, phenyl mercuric acetate, endothall, biuret, technical chlordane, dimethyl 2,3,5,6-tetrachlorotetephthalate, diquat, erbon, DNC, DNBP, dichlorobenil, CPA, diphenamid, dipropalin, trifluralin, solan, dicryl, merphos, DMPA, DSMA, MSMA, potassium azide, acrolein, benefin, bensulfide, AMS, bromacil, 2-(3,4-dichlorophenyl)-4-methyl-1,2,4-oxadiazolidine-3,5-dine, bromoxynil, cacodylic acid, CMA, CPMF, cypromid, DCB, DCPA, dichlone, diphenatril, DMTT, DNAP, EXD, ioxynil, isocil, potassium cyanate, MAA, MAMA, MCPES, MCPP, MH, molinate, NPA, paraquat, PCP, picloram, DPA, PCA, pyrichlor, sesone, terbacil, terbutol, TCBA, LASSO, planavin, sodium tetraborate, calcium cyanamide, DEF, ethyl xanthogen disulfide, sindone, sindone B, propanil and the like. Such herbicides can also be used with the compositions of this invention in the form of their salts, esters, amides, and other derivatives whenever applicable to the particular parent compounds.

g. Examples of Herbicidal Control

The following examples illustrate the method of controlling the weeds described herein. These examples were conducted under standard laboratory conditions, using standard laboratory procedures.

EXAMPLE III

When the compound of 3-[5-[1-(4-chlorophenoxy)ethyl]-1,3,4-thiadiazol-2-yl]-4-hydroxy-1-methyl-2-imidazolidinone (Example 1) was applied preemergence at five pounds per acre to the weed species: *Sida spinosa* (teaweed), *Sesbania* spp. (coffee weed), *Echinochola crusgalli* (L) (barnyardgrass), *Avena fatua* (L) (wild oats), *Abutilon theophrosti* (L) (velvetleaf), *Sorghum halepense* (L) (johnsongrass), *Digitaria sanguinalis* (L) (crabgrass), *Setaria gla ca* (L) (yellow foxtail), at the end of twenty-one days many of the weeds were so severly injured that they could not recover, and others were killed.

EXAMPLE IV

When the compound 3-[5-(1-phenoxymethyl)-2,3,4-thiadiazol-2-yl]-4-hydroxy-1-methyl-2-imidazolidinone, which was prepared in a manner similar to that of the compound of Example I was applied to the same weed species under the same conditions as in Example III, all of the weed species were growing.

While the invention has been described with reference to the specific details of certain illustrative embodiments it is not intended that it shall be limited thereby accept so far as such details appear in the accompanying claims.

I claim:

1. A compound graphically represented by Formula I

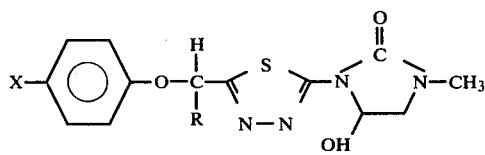

wherein:
X is chlorine, bromine, fluorine or iodine, and
R is an alkyl of up to four carbon atoms,
an alkenyl of up to three carbon atoms,
an alkynyl of up to three carbon atoms, or
a haloalkyl selected from the group consisting of chloromethyl, bromomethyl, 2-chloroethyl, and 2-bromoethyl.

2. The compound as recited in claim 1 wherein R is an alkynyl of up to three carbon atoms.

3. The compound as recited in claim 1 wherein R is an alkenyl of up to three carbon atoms.

4. The compound as recited in claim 1 wherein R is a halo alkyl selected from the group consisting of chloromethyl, bromomethyl, 2-chloroethyl, and 2-bromoethyl.

5. The compound as recited in claim 1 wherein R is a haloalkyl selected from the group chloromethyl and bromomethyl.

6. The compound as recited in claim 1 wherein R is an alkyl of up to four carbon atoms.

7. The compound as recited in claim 1 wherein R is an alkyl selected from the group consisting of methyl, ethyl, and propyl.

8. The compound as recited in any of claims 1, 2, 3, 4, 5, 6, or 7, wherein X is bromine.

9. The compound as recited in any of claims 1, 2, 3, 4, 5, 6, or 7, wherein X is chlorine.

10. The compound as recited in claim 1, which is 3-[5-[1-(4-chlorophenoxy)propyl]-1,3,4-thiadiozol-2-yl]-4-hydroxy-1-methyl-2-imidazolidinone.

11. The compound as recited in claim 1, which is 3-[5-[1-(4-chlorophenoxy)ethyl]-1,3,4-thiadiozol-2-yl]-4-hydroxy-1-methyl-2-imidazolidinone.

12. A method of controlling weeds, which comprises contacting the weeds with a herbicidally effective amount of a compound graphically represented by formula I

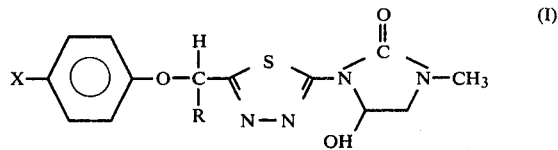

wherein:
X is chlorine, bromine, fluorine or iodine, and
R is an alkyl of up to four carbon atoms, an alkynyl of up to three carbon atoms, an alkenyl of up to three carbon atoms, or a haloalkyl selected from the group consisting of chloromethyl, bromomethyl, 2-chloroethyl and 2-bromoethyl.

13. The method as recited in claim 12, wherein the weeds are of a genus selected from the group consisting of Sida, Datura, Setaria, Digitaria, Sorghum, Sesbania, Abutilon, Ipomoea, Avena, and Echinochola.

14. The method as recited in claim 12, wherein the weeds are of a species selected from the group consisting of *Sida spinosa* (L), *Datura stramonium* (L), *Setaria glauca* (L), *Digitaria sanguinoles* (L), *Sorghum halepense* (L), *Sesbania* spp., *Abutilon theophrasti* (L), *Ipomoea purpurea* (L), Roth, *Avena fatua* (L), and *Echinochola crusgalli* (L).

15. The method as recited in claim 12 wherein the weeds are contacted preemergence.

16. The method as recited in any of claim 12, 13, 14, or 15 wherein R is an alkynyl of up to three carbon atoms.

17. The method as recited in any of claims 12, 13, 14, or 15 wherein R is an alkenyl of up to three carbon atoms.

18. The method as recited in any of claims 12, 13, 14, or 15 wherein R is a haloalkyl.

19. The method as recited in any of claims 12, 13, 14, or 15 wherein R is a haloalkyl selected from the group consisting of chloromethyl and bromomethyl.

20. The method as recited in any of claims 12, 13, 14, or 15 wherein R is an alkyl of up to four carbon atoms.

21. The method as recited in any of claims 12, 13, 14, or 15 wherein R is an alkyl selected from the group consisting of methyl, ethyl and propyl.

22. The method as recited in any of claims 12, 13, 14, or 15, wherein X is chlorine.

23. The method as recited in claim 21 wherein X is a halogen selected from the group consisting of chlorine and bromine.

24. The method as recited in any of claims 12, 13, 14, or 15, wherein the compound is 3-[5-[1-(4-chlorophenoxy)propyl]-1,3,4-thiadiazol-2-yl]-4-hydroxy-1-methyl-2-imidazolidinone.

25. The method as recited in any of claims 12, 13, 14, or 15 wherein the compound is 3-[5-[1-(4-chlorophenoxy)ethyl]-1,3,4-thiadiazol-2-yl]-4-hydroxy-1-methyl-2-imidazolidinone.

* * * * *